US005769635A

United States Patent [19]
Eldreth

[11] Patent Number: 5,769,635
[45] Date of Patent: Jun. 23, 1998

[54] SALIVA EJECTOR BITE BLOCK

[76] Inventor: Mary Anne Eldreth, 6340 Whispering Oaks Dr. N., Jacksonville, Fla. 32277

[21] Appl. No.: 805,135

[22] Filed: Feb. 24, 1997

[51] Int. Cl.$^6$ .................................................. A61C 17/06
[52] U.S. Cl. .............................................. 433/93; 433/140
[58] Field of Search .............................. 433/93, 138, 140

[56] References Cited

U.S. PATENT DOCUMENTS 1,122,086  12/1914  Dunlop ..................................... 433/140
4,024,642  5/1977  Zorovich .................................. 433/93

Primary Examiner—John J. Wilson
Attorney, Agent, or Firm—Arthur G. Yeager

[57] ABSTRACT

A dental appliance includes a circular ring member and two laterally extending rigid arm members which have bite pads on the ends thereof. The circular ring member includes an opening therethrough sized to slidably mount a saliva ejector. The arm members and the ring member are dimensioned to minimize the obstruction of the field of view of the mouth of a dental professional.

18 Claims, 1 Drawing Sheet

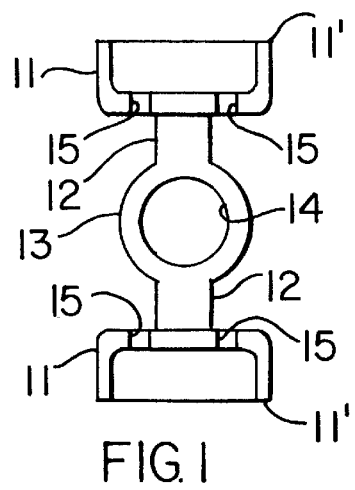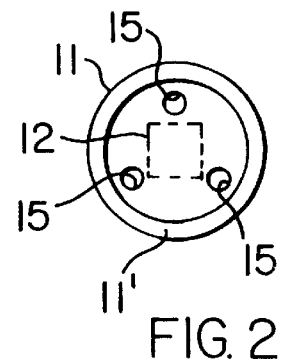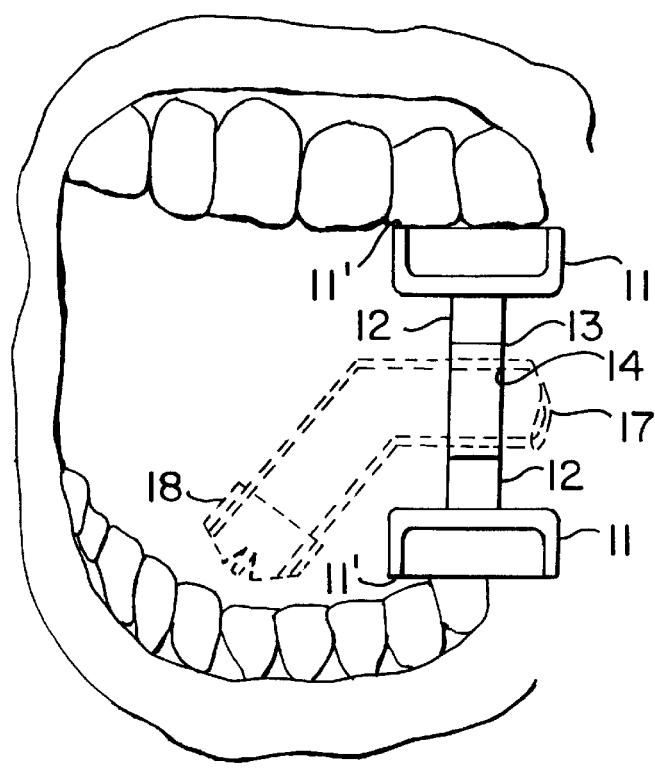

SALIVA EJECTOR BITE BLOCK

BACKGROUND OF THE INVENTION

1. Field of the Invention

The present invention pertains to dental appliances and particularly to removable saliva ejector biting blocks and mouth rests.

2. Prior Art

Bite blocks used as mouth rests are well known to dentistry. The devices, however, tend to be physically large and cumbersome and the devices tend to obstruct the view of the mouth—"the working field"—of the dental professional. In addition, many of the devices are not easily usable by a dental professional who is working without an assistant and they are not very stable in cooperation with lip, tongue and gag reflexes. Accordingly, the saliva ejector is not always positioned for optimum fluid and debris removal. Examples of the prior art that exhibit these limitations include U.S. Pat. Nos. 3,090,122; 3,924,333; 4,354,837; 4,802,851; 5,232,362 and Des. 358,888.

SUMMARY OF THE INVENTION

In one aspect of the present invention there is provided a dental apparatus for insertion into the mouth of a patient during a dental procedure by a person comprising an elongated body having a longitudinal axis and opposite end portions, a pair of bite pads extending laterally of the axis and being respectively attached to the end portions for respective engagement by the upper and lower jaws of a patient. A first attaching means is located generally medially of the body for removably securing a tube of a saliva and debris ejector thereto and positionable in the mouth of a patient. The body has a narrow arm extending between each pad and the first attaching means to maximize visual field of a mouth to the person performing a dental procedure. Other aspects of the invention include the first attaching means including a substantially circular ring member defining an opening therethrough, the opening being sized to slidably engage a tube of an ejector. Each bite pad is formed of deformable material for engaging teeth of a patient. Each bite pad also has a plurality of spaced openings for drainage of fluid and debris therefrom. The ring member is generally planar in shape and dimensioned for maximizing visual field of a mouth to a person performing a dental procedure. The arm members are formed of a solid material to minimize the bending of either of the arm members when the apparatus is being used to hold a patient's mouth open.

Each bite pad is cup shaped and generally semi-hemispherical. The arm members are formed of a rigid material to resist bending of either of the arm members when the apparatus is in use. The first attaching means includes a passageway through the body member, the passageway being sized to slidably engage an ejector tube therein and the passageway is substantially circular in shape.

BRIEF DESCRIPTION OF THE DRAWINGS

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings, in which:

FIG. 1 is a top diagrammatic view of the saliva ejector bite block in accord with the present invention;

FIG. 2 is an enlarged end view of the block of FIG. 1; and

FIG. 3 is a pictorial view of the invention of FIG. 1 placed in a patient's mouth.

DETAILED DESCRIPTION OF THE PREFERRED EMBODIMENT

The present invention relates to a dental appliance and more specially a mouth rest that stabilizes a saliva ejector; a flexible hollow suction tube with a terminal cap secured to one end of the tube. The present invention is unique from all others in that in can be at the fingertips of the dental professional at all times even when it is not in use. Another unique aspect of the present device is that it allows for minimal obtrusion within the mouth thus providing a clear working field, operator ease and patient comfort. The device can be placed anywhere in the mouth such that the upper and lower dental arches come together to secure the device in place. In most cases the device will be secured by opposing teeth, but in the cases of edentulous areas the invention can be secured by the dental ridge.

The saliva ejector is the preferred oral vacuum system. It is used most exclusively by a dental professional when "two hand dentistry" is being done; a dental professional is working alone without the help of an assistant. Lip, tongue and gag reflexes inhibit stabilization of the saliva ejector. The soft tissue of the mouth is many times vacuumed into the openings of the saliva ejector terminal cap inhibiting adequate removal of mouth fluids and debris as well as causing patient discomfort. The present device provides a means of stabilizing the saliva ejector while positioning the saliva ejector such that optimal fluid and debris removal is obtained while maintaining patient comfort.

The value and uniqueness of the device according to the present invention is its ease of use, the clear working field it provides, patient comfort and low cost for disposable use. The disposability is important in avoiding cross contamination. The device is put on to the saliva ejector at the start of the procedure. The saliva ejector is then placed into the vacuum hose. The device is then secure on the saliva ejector in place with no chance of sliding into the mouth as the opening within the device for placement of the saliva ejector is smaller than the saliva ejector terminal cap as well as vacuum hose attachment. The invention can be kept at the vacuum hose end of the saliva ejector without hampering use of the saliva ejector until such time that the device needs to be placed within the mouth. Stabilizing the saliva ejector when needed and yet having the device out of the way when free use of the saliva ejector is preferred provides that the device is uniquely at the fingertips of the dental professional at all times.

With respect now to the drawings, the bite block, according to the present invention is illustrated generally at numeral 10 in FIG. 1. A pair of bite pads 11, having lips 11' are attached to the ends of two elongate narrow rest arms 12 that meet at the center ring member 13. The opening 14 in the ring member 13 is sized to provide a tight fit for a flexible hollow suction tube 17 with a terminal cap (shown in broken lines) to allow the device to be moved on the ejector. Openings 15 which may be of any number and size as appropriate provide for drainage of saliva and debris from inside the bite pads 11 (FIG. 2).

Rest arms 12, which are preferably square but may be of another shape, are sized to be narrow so that they will not block the view of the dental professional as do the devices of the prior art.

FIG. 3 illustrates the use of the device with a patient 16. The device comes in several sizes to accommodate various sizes of mouths and various placement positions of the device within the mouth as may be appropriate in the circumstances. Preferably, the entire device is molded as a single piece of plastic of suitable material for dental apparatus.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A dental apparatus for insertion into the mouth of a patient during a dental procedure by a person comprising an elongated body having a longitudinal axis and opposite end portions, a pair of bite pads extending laterally of said axis and being respectively attached to said end portions for respective engagement by the upper and lower jaws of a patient, first attaching means located generally medially of said body for removably securing a tube of saliva and debris ejector thereto and positionable in the mouth of a patient, said body having a narrow arm extending between each said pad and said first attaching means to maximize visual field of a mouth to the person performing a dental procedure, each said bite pad having a plurality of spaced openings for drainage of fluid and debris therefrom.

2. The dental apparatus as defined in claim 1 wherein said first attaching means includes a substantially circular ring member defining an opening therethrough, said opening being sized to slidably engage a tube of an ejector.

3. The dental apparatus as defined in claim 2 wherein said ring member is generally planar in shape and dimensioned for maximizing visual field of a mouth to a person performing a dental procedure.

4. The dental apparatus as defined in claim 2 wherein said arm members are formed of a rigid material to resist bending of either of said arm members when said apparatus is in use.

5. The dental apparatus as defined in claim 1 wherein each said bite pad is formed of deformable material for engaging teeth of a patient.

6. The dental apparatus as defined in claim 1 wherein said arm members are formed of a solid material to minimize the bending of either of said arm members when said apparatus is being used to hold a patient's mouth open.

7. The dental apparatus as defined in claim 1 wherein each said bite pad is cup shaped and generally semi-hemispherical.

8. The dental apparatus as defined in claim 1 wherein said first attaching means includes a passageway through said body member, said passageway being sized to slidably engage an ejector tube therein.

9. The dental apparatus as defined in claim 8 wherein said passageway is substantially circular in shape.

10. A dental apparatus for removal of fluid and debris from the mouth of a patient during a dental procedure comprising first means for removably securing an ejector apparatus used for the removal of fluid and debris from the mouth to said appliance, and second means for securing said appliance inside the mouth of a patient, said second means including a pair of elongate arm members each having opposite end portions, one of each said end portions being attached to said first means and extending laterally outwardly therefrom, a pair of bite pads for engaging the jaws of a patient, one said pad being attached to the other said end portion of a respective said arm member, said arm members being dimensioned narrowly to minimize the blockage of the visual field of the mouth presented by said arm members to a user of said appliance, each said bite pad having a plurality of spaced openings for drainage of fluid and debris therefrom.

11. The dental apparatus as defined in claim 10 wherein said first means includes a substantially circular ring member defining an opening therethrough, said opening being sized to slidably engage a tube of an ejector.

12. The dental apparatus as defined in claim 11 wherein said ring member is generally planar in shape and dimensioned for maximizing visual field of a mouth to a person performing a dental procedure.

13. The dental apparatus as defined in claim 11 wherein said arm members are formed of a rigid material to resist bending of either of said arm members when said apparatus is in use.

14. The dental apparatus as defined in claim 10 wherein each said bite pad is formed of deformable material for engaging teeth of a patient.

15. The dental apparatus as defined in claim 10 wherein said arm members are formed of a solid material to minimize the bending of either of said arm members when said apparatus is being used to hold a patient's mouth open.

16. The dental apparatus as defined in claim 10 wherein each said bite pad is cup-shaped and generally semi-hemispherical.

17. The dental apparatus is defined in claim 10 wherein said first attaching means includes a passageway through said body member, said passageway being sized to slidably engage an ejector tube therein.

18. The dental apparatus as defined in claim 17 wherein said passageway is substantially circular in shape.

* * * * *